United States Patent [19]
Kuwada et al.

[11] Patent Number: 5,636,136
[45] Date of Patent: Jun. 3, 1997

[54] MEASUREMENT TIME SHORTENING METHOD FOR A MEASUREMENT APPARATUS

[75] Inventors: Atsushi Kuwada, Kusatsu; Tatumi Toida, Tsukuba, both of Japan

[73] Assignee: Daikin Industries, Ltd., Japan

[21] Appl. No.: 338,597

[22] PCT Filed: Mar. 18, 1994

[86] PCT No.: PCT/JP94/00439

§ 371 Date: Dec. 28, 1994

§ 102(e) Date: Dec. 28, 1994

[87] PCT Pub. No.: WO94/22019

PCT Pub. Date: Sep. 29, 1994

[30] Foreign Application Priority Data

Mar. 18, 1993 [JP] Japan .................................. 5-058986

[51] Int. Cl.⁶ .................................................. G06F 17/00
[52] U.S. Cl. ............................ 364/500; 364/497; 364/569
[58] Field of Search .................................. 364/500, 502, 364/569, 496, 223.4, 924.3, 497; 436/50; 422/36

[56] References Cited

U.S. PATENT DOCUMENTS

| | | | |
|---|---|---|---|
| 5,282,149 | 1/1994 | Grandome et al. | 364/497 |
| 5,380,487 | 1/1995 | Choperena et al. | 422/36 |

FOREIGN PATENT DOCUMENTS

| | | |
|---|---|---|
| 359049 | 3/1990 | European Pat. Off. |
| 63-32367 | 2/1988 | Japan. |
| 3-72236 | 3/1991 | Japan. |

OTHER PUBLICATIONS

Field et al., "Overlapped Processing in Wet Chemical Analyzer" IBM Technical Disclosure Bulletin, vol. 19, No. 3, Aug. 1976, pp. 1022–1024.

*Primary Examiner*—Emanuel T. Voeltz
*Assistant Examiner*—M. Kemper
*Attorney, Agent, or Firm*—Beveridge, DeGrandi, Weilacher, Young, L.L.P.

[57] ABSTRACT

In a measurement apparatus which performs reaction processings of plural measurement units in a timely overlapped manner, a predetermined time for performing the reaction processing is previously determined, pre-processings are divided when a sum time of required times for performing the plural pre-processings with a pre-processing apparatus is longer than predetermined time. Prior pre-processings among the divided pre-processings are then performed in package prior to the series of processings, so that a required time for the plural measurement units in the measurement apparatus is shortened.

3 Claims, 19 Drawing Sheets

MEASUREMENT TIME SHORTENING METHOD FOR A MEASUREMENT APPARATUS

TECHNICAL FIELD

The present invention relates to a measurement apparatus, more particularly to a measurement apparatus which includes plural measurement units and carries out various measurements in an overlapped manner over the passage of time.

BACKGROUND ART

In the past, an optical measurement method has been known for a measurement apparatus. The method employs a slab-type optical waveguide. The method excites labeled fluorescent bodies which exist in the vicinity of the surface of the optical waveguide using evanescent wave components from the optical waveguide. To actualize the optical measurement method, an apparatus is proposed as is illustrated in FIG. 15. In the apparatus, a test liquid housing chamber 92 is formed in one body at one face of a slab-type optical waveguide 91. An exciting light radiated from a laser light source or the like, which is not illustrated, enters into the optical waveguide 91 through a dichroic mirror 93. Fluorescent light radiated from labeled fluorescent bodies exits through the optical waveguide 91, and is radiated by the dichroic mirror 93 so as to be introduced into a detector 95 through an optical filter 94.

When the above-mentioned arrangement is employed, antibodies 96 are previously fixed on a surface of the optical waveguide 91. Antigens 97 in a test liquid are then bound by the antibodies 96, and then fluorescent labeled antibodies 98 (which are made by labeling antibodies with fluorescent bodies) are bound by the antigens 97. That is, the quantity of bound fluorescent labeled antibodies 98 is determined based upon the quantity of antigens 97 in the test liquid. And, an evanescent wave component is obtained by introducting an exciting light into the optical waveguide 91. Only the label fluorescent bodies 98a of the bound fluorescent labeled antibodies 98 are excited by the evanescent wave component so that the label fluorescent bodies 98a radiate fluorescence. Therefore, the intensity of radiated fluorescence is in proportion to the quantity of the antigens 97 in the test liquid. Further, the fluorescence is guided in the optical waveguide 91. Consequently, existence or non-existence or a degree of immnoreaction is measured by reflecting only the guided fluorescence by the dichroic mirror 93, cutting off the exciting light component with the optical filter 94, and introducing the fluorescence into the detector 95.

To perform an immunological measurement using the fluorescence immunological measurement apparatus having the above-mentioned arrangement, pre-processing for diluting the test liquid including antigens 97 with a dilution liquid is necessary prior to housing the test liquid and the fluorescent labeled antibodies 98 in the test liquid housing chamber 92.

FIG. 16 is a diagram explaining a conventional method employed in a fluorescence immunological measurement apparatus having six measurement units when the above-mentioned immunity measurement is carried out. In FIG. 16, T1 represents a preparation time until the beginning of a primary reaction, that is, a preparation time until the diluted test liquid is poured in the test liquid housing chamber 92 acting as a reaction vessel. T2 represents the primary reaction time of the immunological reaction, that is, a reaction time for the reception of the antigens 97 in the test liquid by the antibodies 96 which were previously fixed on the surface of the test liquid housing chamber 92. T3 represents a time period from B/F separation to the beginning of a secondary reaction, that is, a time period for discharging the test liquid in the test liquid housing chamber 92 and for pouring reagent which includes fluorescent labeled antibodies 98 in the test liquid housing chamber 92. T4 represents a light measurement time, that is, a time for measuring the fluorescence radiated by the label fluorescent bodies 98a of the fluorescent labeled antibodies 98 which have been received by the antigens 97. In the fluorescent immunological measurement apparatus, when measurement of the six measurement units is carried out using one pouring apparatus and one measurement data detection system, the preparation time T1 and the primary reaction time T2 must satisfy the equation of $T1 \times 5 \leq T2$, because two measurement units cannot be processed simultaneously.

But, the preparation time T1 greatly varies depending upon the content of the pre-processing assigned to the measurement units, that is, the content of the diluting processing of a test liquid.

Hereinafter, great variation of the preparation time T1 is specifically described by taking different cases as examples. One case is a case where a dilution magnification of a test liquid is determined to be about 50 times, which is a standard dilution magnification (hereinafter referred to as case A). Another case is a case where dilution magnification of A test liquid is determined to be about 50×50=2500 times, for example (hereinafter referred to as case B). A further case is a case where the quantity of the test liquid is great and the waste quantity caused by stirring the liquid in another vessel and sucking the liquid from the other vessel is required to be less (hereinafter referred to as case C).

In the case A, a dilution liquid is sucked from a dilution liquid vessel and a test liquid is sucked from a test liquid vessel. The sucked dilution liquid and test liquid the are poured into a stirring vessel, and both liquids are stirred in the stirring vessel so that the test liquid is diluted. Thereafter, the diluted test liquid in the stirring vessel is sucked and poured into a test liquid housing chamber 92 which is used as a reaction vessel so that preparation for measurement is performed. A required time for these processings is 80 seconds.

In the case B, a buffer liquid stored in a bottle or the like is sucked and a test liquid in a test liquid vessel is sucked, and the buffer liquid and the test liquid are discharged and stirred in a stirring vessel so as to generate a first diluted test liquid (for example, a 50-times diluted test liquid). Such processings are a first stage. Then, the buffer liquid stored in the bottle or the like is sucked, the first diluted liquid and the buffer liquid are discharged into a multi-function vessel and are stirred so as to generate a second diluted liquid (for example, 50-times×50-times=2500-times). In these processings, a required time for generating the first diluted liquid is 50 seconds, and a required time for generating the second diluted liquid from the first diluted liquid is 80 seconds. Therefore, 130 seconds is required for all of the processings.

In the case C, a dilution liquid is sucked from a dilution liquid vessel and a test liquid is sucked from a test liquid vessel, and the sucked dilution liquid and test liquid are discharged into a test liquid housing chamber 92 which is used as a reaction vessel. Both liquids are stirred for diluting the test liquid so that preparation for measurement is performed. A required time for these processings is 60 seconds.

When the case A, case B and case C exist in a mixed condition, the required time of 130 seconds of the case B which takes the longest time for diluting processing should be determined to be the standard required time for carrying out measurements using six measurement units. From the relationship of T1×5≦T2, the relationship of 130 seconds× 5≦650 seconds is obtained whereby the primary reaction time T2 should be determined to be mope than 650 seconds.

However, 650 seconds is much longer than 420 second {80 seconds×5+20 seconds (margin)=420 second, including a little margin to avoid to overlap of T1 and T3} for six measurement units. A disadvantage arises in that a measurement time of a measurement apparatus becomes longer. It will be described in detail with reference to FIGS. 16–19 that a measurement time becomes longer.

[When six of case A types are measured]

FIG. 16 is a timechart for when a time interval between measurement units is determined to be 80 seconds and six case A types are measured.

In the first measurement unit, T1=80 seconds, T2=650 seconds (fixed), T3=80 seconds, T4=70 seconds, and a total time becomes 880 seconds. And, to finish measurement from the first measurement unit to sixth measurement unit, measurements are carried out 5 times and every 80 seconds sequentially after the first measurement unit for every measurement. Therefore, a measurement time till a measurement by the sixth measurement unit will be finished is necessarily 880 seconds+80 seconds×5=1280 seconds.

[When three case B types are measured]

FIG. 17 is a timechart for when three case B types are measured. In the first measurement unit, T1=130 seconds, T2=650 seconds (fixed), T3=80 seconds, T4=70 seconds, and a total time becomes 930 seconds. Further, a preparation time T1 of case B is 130 seconds and is longer than a required time T3 of 80 seconds, therefore a processing of T3 for a prior measurement unit is carried out during a preparation time T1 for next measurement unit. And, measurements are carried out 2 times at 130 second intervals sequentially after the first measurement unit for every measurement. Therefore, a measurement time until a measurement by the third measurement unit will be finished is necessarily 930 seconds+130 seconds×2=1190 seconds.

[When six case B types are measured]

FIG. 18 is a timechart for when six case B types are measured. In the first measurement unit, T1=130 seconds, T2=650 seconds (fixed), T3=80 seconds, T4=70 seconds, and a total time becomes 930 seconds. And, to finish the measurements from the first measurement unit to the sixth measurement unit, measurements are carried out 5 times and every 130 seconds sequentially after the first measurement for every measurement. Therefore, a measurement time till a measurement by the sixth measurement unit will be finished is necessarily 930 seconds+130 seconds×5=1580 seconds.

[When three case B types and three case C types are measured]

FIG. 19 is a timechart for when three case B types and three case C types are measured. In this case, it is assumed that three case C types are measured, and then three case B types are measured. In the first measurement unit, T1=60 seconds (a preparation time for case C), T2=650 seconds (fixed), T3=80 seconds, T4=70 seconds, and a total time becomes 860 seconds. And, time T3 of 80 seconds is longer than the preparation time T1 for case C from the first to third measurement units, thereby measurements are carried out by determining a time interval between measurement units to be 80 seconds. From the fourth to the sixth measurement units, processing of T3 is carried out within 130 seconds, which is the preparation time T1 for case C. Therefore, a measurement time for finishing measurements by the first to the sixth measurement units is necessarily 860 seconds+80 seconds×3+130 seconds×2=1380 seconds.

When a primary reaction time T2 is determined to suit a measurement content which requires maximum preparation time as was described earlier, the measurement time becomes extremely longer for measurements of various combinations. A disadvantage arises in that the efficiency of measurement is lowered.

In the foregoing, the description was made by taking a fluorescent immunity measurement apparatus as a measurement apparatus. Disadvantages which are similar to that of the above-mentioned fluorescent immunity measurement apparatus arise when a pre-processing and an after-processing are necessary and the pre-processing and the after-processing are carried out using a single processing apparatus in a measurement apparatus which performs measurement based upon absorption, diffusion, or polarization, or in a measurement apparatus utilizing bonding reaction other than an antigen-antibody reaction or a catalytic reaction such as an enzyme-reaction, because the processing apparatus cannot be used for plural measurement units simultaneously when measurements are carried out using plural measurement units sequentially.

DISCLOSURE OF THE INVENTION

The present invention was made to solve the above-mentioned problems. It is an object of the present invention to provide a measurement time shortening method for a measurement apparatus which can shorten an entire measurement time for the measurement apparatus which includes plural measurement units and carries out various measurements in a timely overlapped manner.

To perform the above-mentioned object, a measurement time shortening method for a measurement apparatus according to claim 1 is a method for previously determining a time for performing a predetermined reaction, for dividing a predetermined pre-processing when a total time required for plural pre-processings performed by an automated processing means is longer than the predetermined time, and for carrying out those prior processings in package, which are prior among the divided pre-processings prior to a series of processings, in a measurement apparatus which includes plural measurement units each of which performs the pre-processing which is a preparation of the predetermined reaction, the predetermined reaction processing, and an after-processing, a single measurement means for obtaining measurement data based upon a phenomenon produced by the predetermined reaction, and the single automated processing means for performing at least the pre-processing and the after-processing, whereby the predetermined reaction processing of the plural measurement units are carried out in a timely overlapped manner.

A measurement time shortening method for a measurement apparatus according to claim 2 is a method for calculating a sum of required time of pre-processings for subsequent measurement units and after-processings for prior measurement units, for carrying out each measurement by determining a longer time as a reaction time among a previously determined minimum reaction time and the calculated sum time, and for correcting measurement data obtained by each measurement unit based upon the correspondingly determined reaction time, in a measurement apparatus which includes plural measurement units each of which performs the pre-processing which is a preparation of a predetermined reaction, a predetermined reaction processing, and the after-processing, a single measurement means for obtaining measurement data based upon a phenomenon occurring to the predetermined reaction, and the single automated processing means for performing at least the pre-processing and the after-processing, the predetermined reaction processing of the plural measurement units being are carried out in a timely overlapped manner.

As to the measurement apparatus according to claim 1, when a sum of required times for plural pre-processings to be carried out by the automated processing means is longer than the predetermined time, the predetermined pre-processings are divided. The prior processings among the divided processings are carried out in package prior to the series of processings. Therefore, the pre-processings are finished by sequentially carrying out the later processings of the divided pre-processings within a previously predetermined time so that the pre-processings and the predetermined reactions can be carried out within the previously determined time, even when a required time for the pre-processing is long. Consequently, the automated processing means never overlaps between the measurement units so that measurement data of all measurement units is obtained with a short measurement time even when the measurement apparatus includes the single automated processing means.

As to the measurement apparatus according to claim 2, for each of the measurements which are carried out sequentially, the sum of the required time of subsequent of following measurement units and required time of after-processing of preceeding measurement units is calculated, and a longer time between a previously determined minimum reaction time and the calculated sum time is determined as a reaction time. Therefore, when a number of measurements is small, the determined reaction time can be shortened so that a total measurement time can be shortened. Further, though measurement data obtained from each measurement unit is corrected based upon the reaction time which is determined correspondingly, measurement accuracy is prevented from lowering even when reaction times for a measurement unit varies from other measurement units.

BEST MODE FOR PERFORMING THE INVENTION

Referring the attached drawings, we explain the present invention in detail.

First, we explain a measurement unit of a fluorescent immunity measurement apparatus in which a measurement time shortening method for the measurement apparatus according to the present invention is applied.

Figure 2:
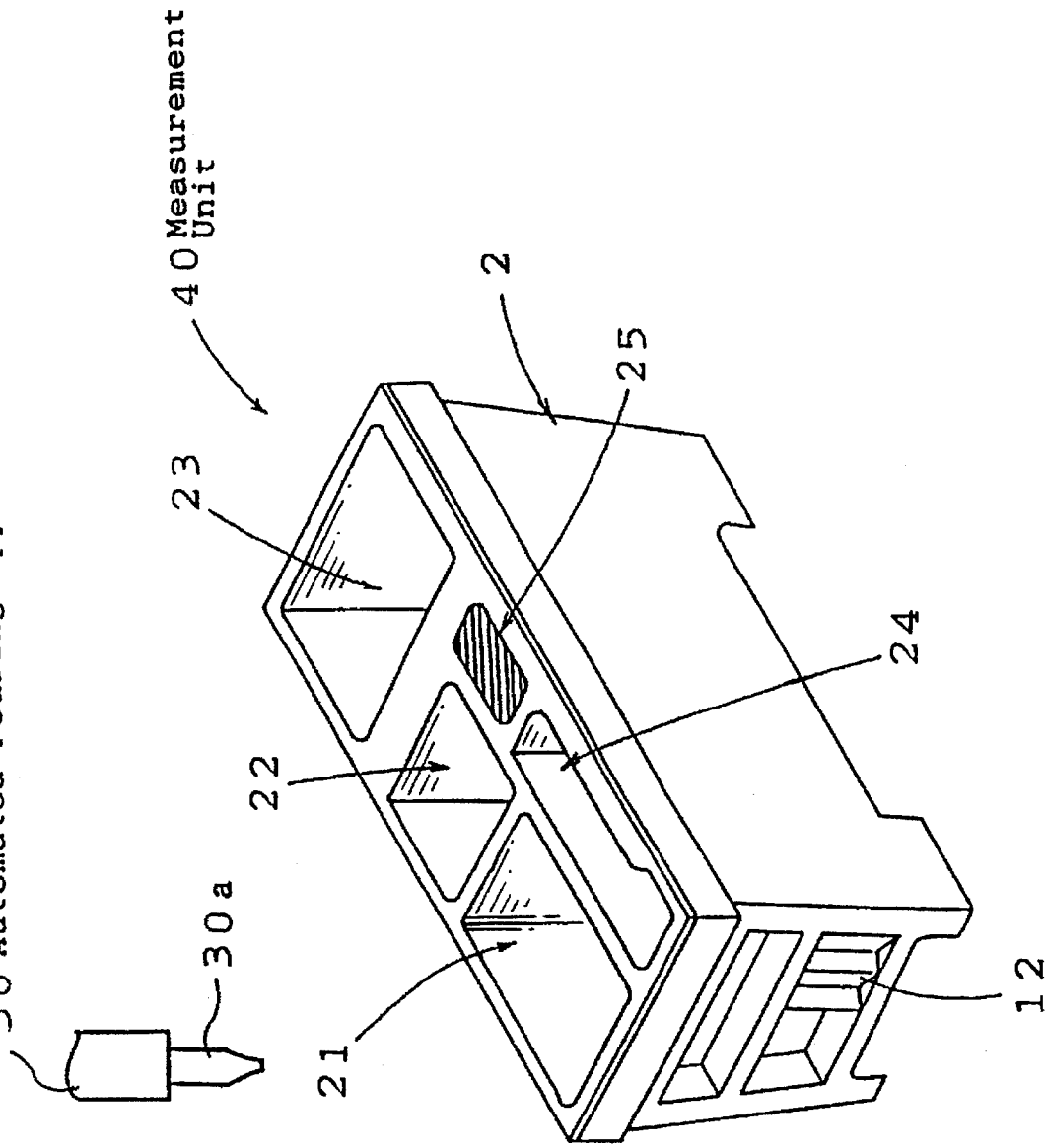
FIG. 2 is a perspective view of a fluorescent immunity measurement apparatus which is used for the present invention.

FIG. 2 is a perspective view illustrating a measurement unit 40. In the measurement unit 40, two pre-processing vessels 21 and 22 are disposed in a longitudinal direction at a predetermined position of a casing 2, and a reaction vessel 24 is disposed in the casing 2 so as to face the entirety of the pre-processing vessel 21 and half of the pre-processing vessel 22. An absorber housing vessel 25, which is filled with absorber, is disposed so as to face the rest of the pre-processing vessel 22 and to be located at the end of the reaction vessel 24. A pre-processing vessel 23 is disposed so as to face the pre-processing vessel 22 and the absorber housing vessel 25. Further, a slab-type optical waveguide 1 is formed over at least a part of a side wall of the reaction vessel 24, and an exciting light introducing prism 12 is formed in correspondence with an edge portion at the reaction vessel side of the slab-type optical waveguide 1. The casing 2 including these pre-processing vessels 21, 22 and 23, the reaction vessel 24, the absorber housing vessel 25, the slab-type optical waveguide 1, the exciting light introducing prism 12 and the like is formed as one body by inflection molding or the like.

When an immunological measurement is carried out using the measurement unit having the above-mentioned arrangement, liquids are housed within the corresponding pre-processing vessels and a reservation liquid for reserving antibodies 96 is housed within the reaction vessel 24. Then, dilution liquid is taken out from the pre-processing vessel 21, and used to dilute a test liquid including antigens 97 in the pre-processing vessel 23, and to dilute a reagent including fluorescent labeled antibodies 98 in the pre-processing vessel 22. The dilution of the reagent may be carried out simultaneously with the dilution of the test liquid, but the dilution of the reagent also may be carried out after the dilution of the test liquid. Then, the diluted test liquid is poured in the reaction vessel 24 so that the antigens 97 are bound by the antibodies 96 fixed on the optical waveguide 1. The test liquid within the reaction vessel 24 is then discharged.

Figure 3:
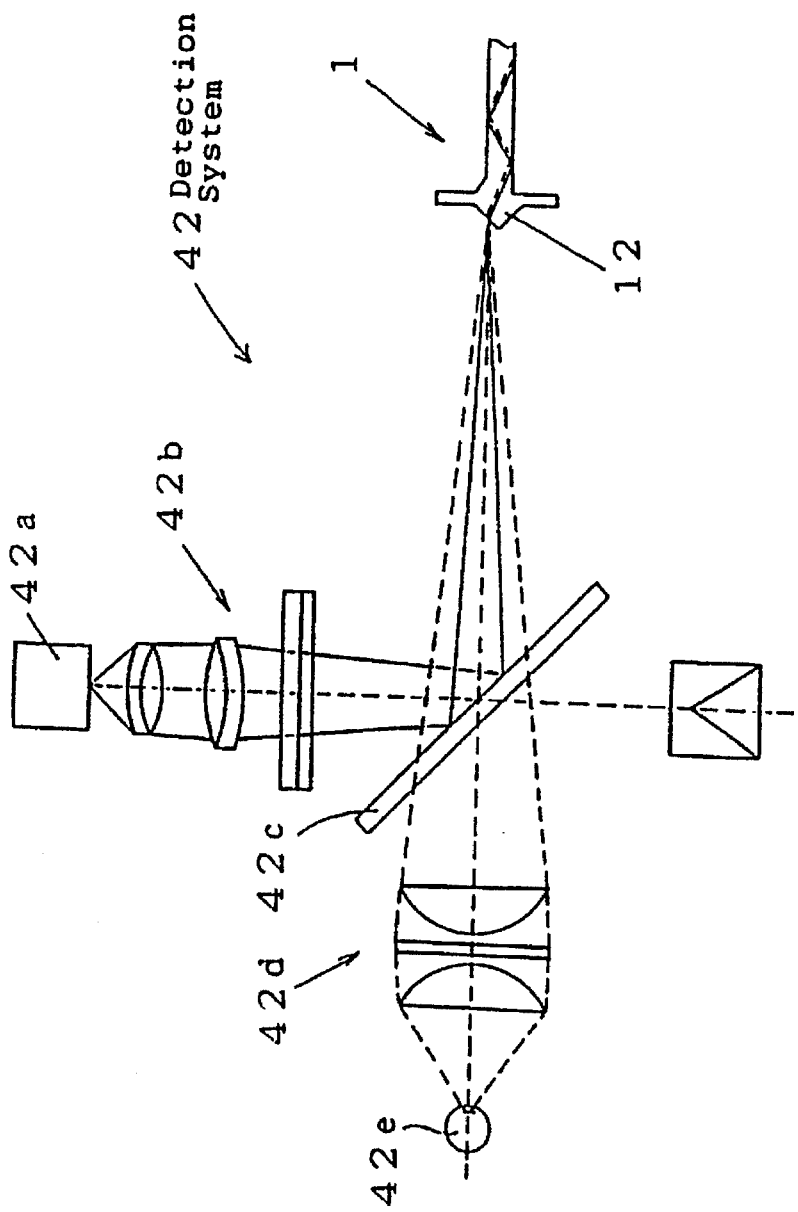
FIG. 3 is a horizontal cross-section view schematically illustrating a detection system of the fluorescent immunity measurement apparatus.

Thereafter, an exciting light output from an exciting light source 42a in a detection system 42 which is illustrated in FIG. 3 is guided to the exciting light introducing prism 12 through an optical system 42b and a dichroic mirror 42c. The test liquid diluted in the pre-processing vessel 21 is poured in the reaction vessel 24 of the casing 2, so that fluorescence corresponding to a quantity of the antigens 97 is obtained That is, when the reagent is poured in the reaction vessel 24 as an after-processing of an antigen-antibody reaction, the fluorescent labeled antibodies 98 in the reagent are bound by the antigens 97 which are in turn bound by the antibodies 96. Therefore a quantity of the fluorescent labeled antibodies 98, which corresponds to the quantity of the antigens in the test liquid, are bound in the vicinity of the surface of the optical waveguide 1.

The exciting light used as a measurement light is refracted by the prism 12 so as to be introduced into the optical waveguide 1. The exciting light propagates by repeating total reflection. Only the label fluorescent bodies 98a of the bound fluorescent labeled antibodies 98 ape excited by an evanescent wave component of the exciting light, so that the label fluorescent bodies 98a radiate a characteristic fluorescence. The radiated fluorescence propagates in the optical waveguide 1 and is output from an exciting light introducing region of the prism 12. The output fluorescence passes through the dichroic mirror 42c which is illustrated in FIG. 3, and is detected by an optical detector 42e through a collecting optical system 42d.

Further, the dilution processing of the test liquid which is the pre-processing of the antigen-antibody reaction and the pouring processing of the reagent which is the after-processing of the antigen-antibody reaction in the measurement unit 40 are carried out by controlling an automated pouring apparatus 30 which includes a predetermined nozzle 30a or the like, as is illustrated in FIG. 2. That is, by using the measurement unit 40 in which each vessel is formed in one body, the pre-processing and the after-processing are carried out by performing a position controlling with a narrow range and a pouring controlling of the automated pouring apparatus 30, and the immunological measurement is performed with ease and with high accuracy.

Figure 1:
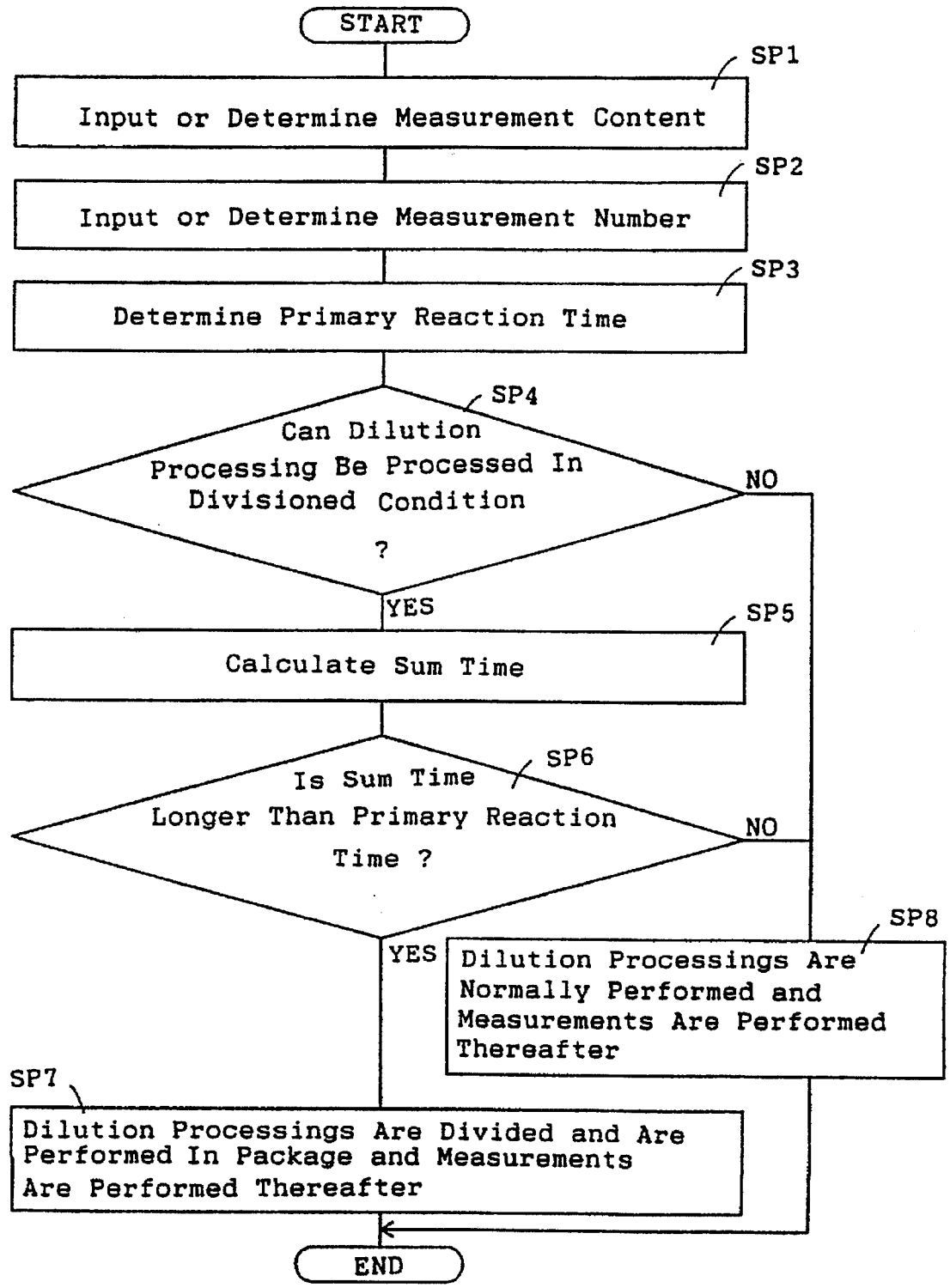
FIG. 1 is a flowchart explaining a measurement method for a fluorescent immunity measurement apparatus as a measurement time shortening method for a measurement apparatus according to a first embodiment of the present invention.

FIG. 1 is a flowchart explaining a measurement method for a fluorescent immunological measurement apparatus as a measurement time shortening method according to first embodiment of the present invention.

The fluorescent immunological measurement apparatus includes plural measurement units 40 which are illustrated in FIG. 2. The fluorescent immunological measurement apparatus measures by measuring fluorescence through the detection system 42 which is illustrated in FIG. 3. The fluorescence is radiated by the label fluorescent bodies 98a of the fluorescent labeled antibodies 98 based upon the antigen-antibodies reaction. The pouring processing for diluting the test liquid, a primary reaction processing, from B/F separation to a secondary reaction processing (after-processing) are automated by using the automated pouring apparatus 30 or the like. In the following description, it is assumed for easy understanding that the fluorescent immunological measurement apparatus includes six measurement units for allowing six measurements in parallel, including one or more of the case A, case B and case C types.

In step SP1, when plural measurements are carried out, a measuring man inputs (or a measurement apparatus determines) which case among the case A, case B and case C are to be measured. In step SP2, the measuring man inputs (or the measuring apparatus determines) a number of measurement of each of the selected cases. In step SP3, a primary reaction time is determined. In step SP4, it is judged whether or not the selected cases include the case B, which allows the dilution processing to be made in a separated manner. When it is judged that the selected cases include the case B, in step SP5, a sum of the required times of the dilution processings for all measurement units based upon the number of measurements of each case which is input is determined. In step SP6, it is judged whether or not the sum time of dilution processing times is longer than the previously determined primary reaction time. When it is judged that the sum time of dilution processing times is longer than the previously determined primary reaction time, in step SP7, the dilution processings for the case B type processings are divided, and the prior dilution processings of the divided dilution processings of carried out in package prior to the dilution processing in the first measurement unit. When it is judged in step SP6 that the sum time of dilution processing times is shorter than a previously determined primary reaction time, In step SP8, division of the dilution processing is not carried out, and the dilution processing is carried out ordinarily for each measurement unit. Also when it is judged in step SP4, that the selcted cases do not include the case B, in step SP8, the dilution processing is carried out ordinarily for each measurement unit.

That is, the characteristic point of this embodiment is that the primary reaction time is previously determined, and only when the sum time of the required times of dilution for plural measurement units is longer than the previously determined primary reaction time, the predetermined dilution processings are divided and prior processings among the divided dilution processings are carried out in package prior to the dilution processing of the first measurement unit.

Specifically, with measurements of the case B type, which are complicated and take a long preparation time T1 until the primary reaction begins, processing in the preparation time T1 is divided into two pouring processings. One pouring processing generates a first diluted test liquid (a required time is 80 seconds) and the other pouring processing generate a second diluted test liquid (a required time is 50 seconds). The pouring processings for generating the first diluted test liquid, which processings are the prior processings among the divided processings, are carried out in package prior to the measurement operation of the first measurement unit. The pouring processings for generating the second diluted test liquid are carried out within the primary reaction time T2. The primary reaction time T2 is accordingly shortened and the entire measurement time is also shortened.

Further, the previously determined primary reaction time T2 is fixed to 420 seconds which is determined by adding a small margin to 400 seconds (80 seconds×5=400 seconds) which is the minimum necessary time to avoid overlap of the pouring processings for the measurement units because the maximum number of measurements is 6. The minimum necessary time is determined by taking the pouring processing time (80 seconds) for generating the diluted test liquid in the case A, the following pouring processing time (80 seconds) for generating the second diluted test liquid in the case B, the pouring processing time (60 seconds) for generating the diluted test liquid in the case C, and the pouring processing time (80 seconds) of T3, into consideration.

In the following, it is described how the measurement method according to this embodiment can make the measurement time shorter, by taking specific measurement configurations including any one of the case A, case B and case C for example.

[When six case A types are measured]

Figure 4:
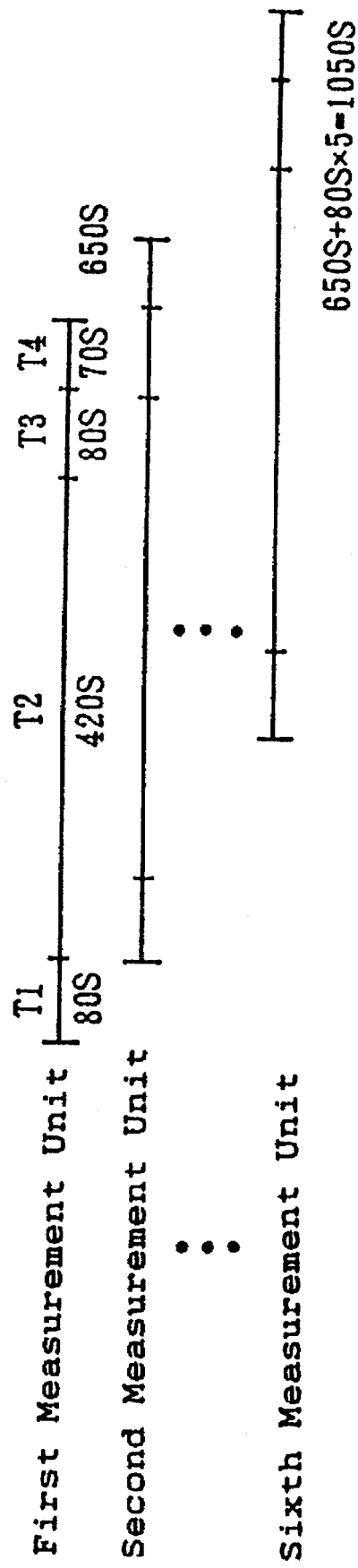
FIG. 4 is a diagram useful in understanding the measurement method of the first embodiment in the measurement time shortening method for the measurement apparatus according to the present invention.

FIG. 4 is a timechart for when six case A types are measured. In this situation, no case B type is included which requires division of the dilution processing. Therefore, for the first measurement unit, T1=80 seconds, T2=420 seconds (fixed), T3=80 seconds, T4=70 seconds, and the total required time is 650 seconds. And to finish the measurement from the first measurement unit to the sixth measurement unit, five measurements are carried out every 80 seconds, corresponding to the dilution processings of the test liquid, sequentially after the dilution in measurement unit is started. Therefore, the required measurement time from the beginning of the measurement in the first measurement unit to the finish of the measurement in the sixth measurement unit is 650 seconds+80 seconds×5=1050 seconds.

[When three case B types are measured]

Figure 5:
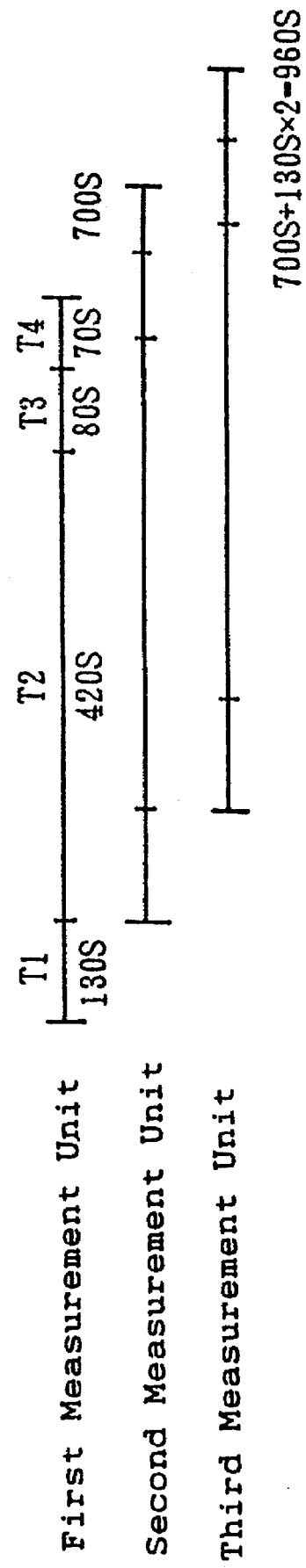
FIG. 5 is a diagram useful in understanding the measurement method of the first embodiment in the measurement time shortening method for the measurement apparatus according to the present invention.

FIG. 5 is a timechart for when three cases B types are measured. In the case B, the dilution processings can be carried out in a divided condition. A total of the preparation times T1 when three cases B are carried out is 130 seconds× 1050 seconds, which is shorter than the previously determined primary reaction time of 420 seconds. Therefore, the dilution processings are not divided but are normally sequentially carried out. For the first measurement unit, T1=130 seconds, T2=420 seconds (fixed), T3=80 seconds, T4=70 seconds, and the total required time is 700 seconds. And to finish the measurements from the first measurement unit to the third measurement unit, each of the two measurements are carried out every 130 seconds sequentially from the measurement of the first measurement unit, because the preparation time T1 is longer than the required time of T3 of 80 seconds. Therefore, the required measurement time from the beginning of the first measurement to the finishing of the third measurement is 700 seconds+130 seconds×2=960 seconds.

[When six case B types are measured]

Figure 6:
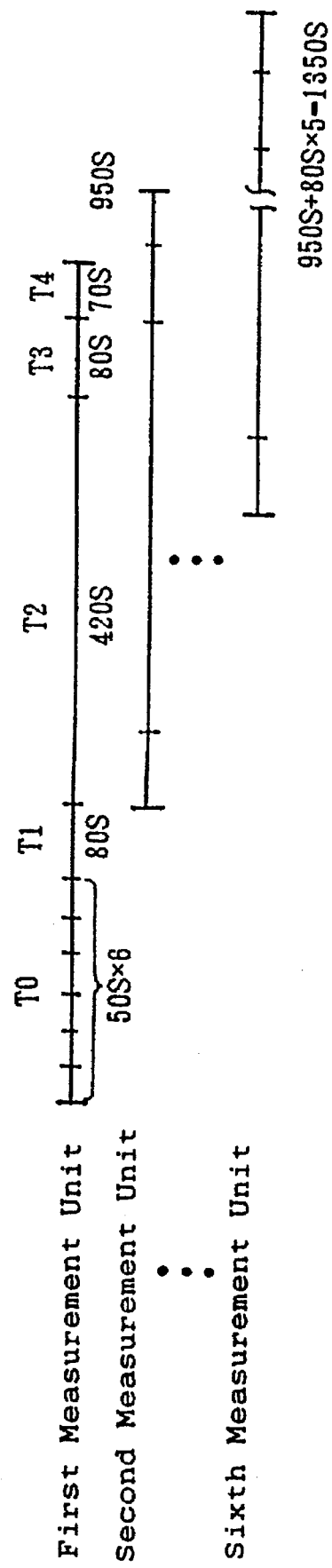
FIG. 6 is a diagram useful in understanding the measurement method of the first embodiment in the measurement time shortening method for the measurement apparatus according to the present invention.

FIG. 6 is a timechart of when six case B types are measured. This situation includes cases B which can have their dilution processings carried out in a divided condition, and the total of the preparation times T1 when six cases B are measured becomes 130 seconds×5=650 seconds, and this is longer than the previously determined primary reaction time of 420 seconds. Therefore, each case B dilution procceeing is divided into 50 seconds for generating the first diluted test liquid and 80 seconds for generating the second diluted test liquid. All 50 seconds for generating the first diluted test liquid for the first measurement unit to the sixth measurement unit are performed in package prior to the measurement time of the first measurement unit. That is, the processing time for generating the first diluted test liquids of T0=50 seconds×6=300 seconds is provided prior to the processing of T1 of the first measurement unit.

Therefore, for the first measurement unit, T0=50 seconds×6=300 seconds, T1=80 seconds, T2=420 seconds (fixed), T3=80 seconds, T4=70 seconds, and the total required time is 950 seconds. And to finish the measurement from the first measurement unit to the sixth measurement unit, five measurements are carried out, each every 80 seconds, by determining the time interval between the measurement units as 80 seconds by taking 80 seconds for generating the second diluted test liquid and 80 seconds of the processing time of T3 into consideration, sequentially from the first measurement. Consequently, the required measurement time from the beginning of the first measurement to the finishing of the sixth measurement becomes 950 seconds+80 seconds×5=1350 seconds.

[When three case B types and three case C types are measured]

Figure 7:
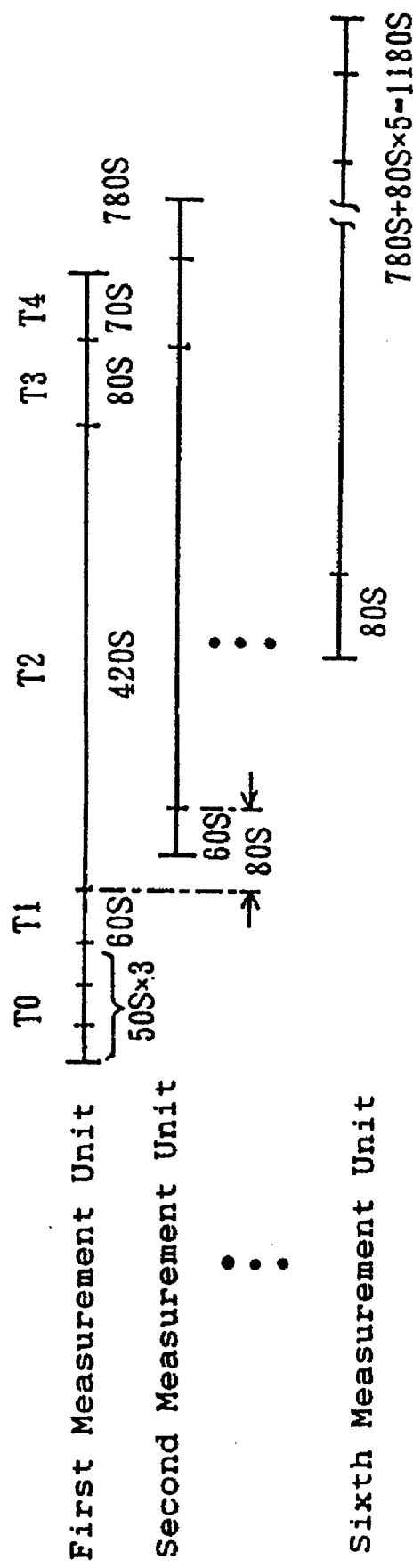
FIG. 7 is a diagram useful in understanding the measurement method of the first embodiment in the measurement time shortening method for the measurement apparatus according to the present invention.

FIG. 7 is a timechart for when three case B types and three case C types are measured. This situation includes cases B in which the dilution processings can be carried out in a divided condition, and the total of the preparation times T1 when three cases B and three cases C are measured becomes 60 seconds×2+130 seconds×3=510 seconds, and is thus longer than the previously determined primary reaction time of 420 seconds. Therefore, each case B is divided into 50 seconds for generating the first diluted test liquid and 80 seconds for generating the second diluted test liquid. All 50 seconds for generating the first diluted test liquid from the first measurement unit to the third measurement unit are performed in package prior to the measurement time of the first measurement unit. That is, the processing time for generating the first diluted test liquids of T0=50 seconds× 3=150 seconds are provided prior to the processing of T1 of the first measurement unit. Therefore, for the first measurement unit, T0=150 seconds, T1=60 seconds (the preparation time for the case C), T2=420 seconds (fixed), T3=80 seconds, T4=70 seconds, and the total required time is 780 seconds. And to finish the measurement from the first measurement to the third measurement, the time interval between the measurements is determined to be 80 seconds, so as not to overlap the processings of the automated pouring apparatus because the dilution time of the case C is 60 seconds and the processing time of T3 is 80 seconds. Further, from the fourth measurement to the sixth measurement, the processing time for generating the first diluted test liquid is 80 seconds and the processing time of T3 is 80 seconds. Therefore, to finish the measurements from the first measurement to the sixth measurement, five measurements are carried out each every 80 seconds sequentially from the first measurement. Consequently, the required measurement time from the beginning of the first measurement to the finishing of the sixth measurement is 780 seconds+80 seconds×5=1180 seconds.

The above-mentioned results are collected in compared condition with the conventional examples in Table 1.

TABLE 1

| | First Embodiment | | Conventional Example | |
| --- | --- | --- | --- | --- |
| | First | Sixth | | |
| Content | Measurement Slot | Measurement Slot | First Measurement Slot | Sixth Measurement Slot |
| Six cases A | 650 sec | 1050 sec | 880 sec | 1280 sec |
| Three cases B | 700 sec | 960 sec | 930 sec | 1190 sec |
| Six cases B Three Cases | 950 sec | 1350 sec | 930 sec | 1580 sec |
| C and Three cases B | 780 sec | 1180 sec | 860 sec | 1360 sec |

As is apparent from the Table 1, this embodiment greatly shortens the measurement time in comparison with the conventional measurement method which is illustrated in FIGS. 16–19.

As is described in the foregoing, with this measurement method, the primary reaction time is fixed at a predetermined time by taking the measurement processes of plural measurement units into consideration. When dilution processing cannot be carried out within the predetermined time, each of the predetermined dilution process is divided into two dilution processings and the divided dilution processings of the first stage are carried out in package prior to the measurement of the first measurement unit. Thereby, the the total measurement time of the measurement apparatus can be shortened.

Further, when an object for measurement is blood or the like which includes components causing precipitation during processing in the preparation time T1, stirring must be carried out first. Though the time of about 20 seconds is added to the preparation time T1, the test liquid is stirred and then divided similar the case B, and the similar measurement processings are carried out.

Second Embodiment

Figure 8:
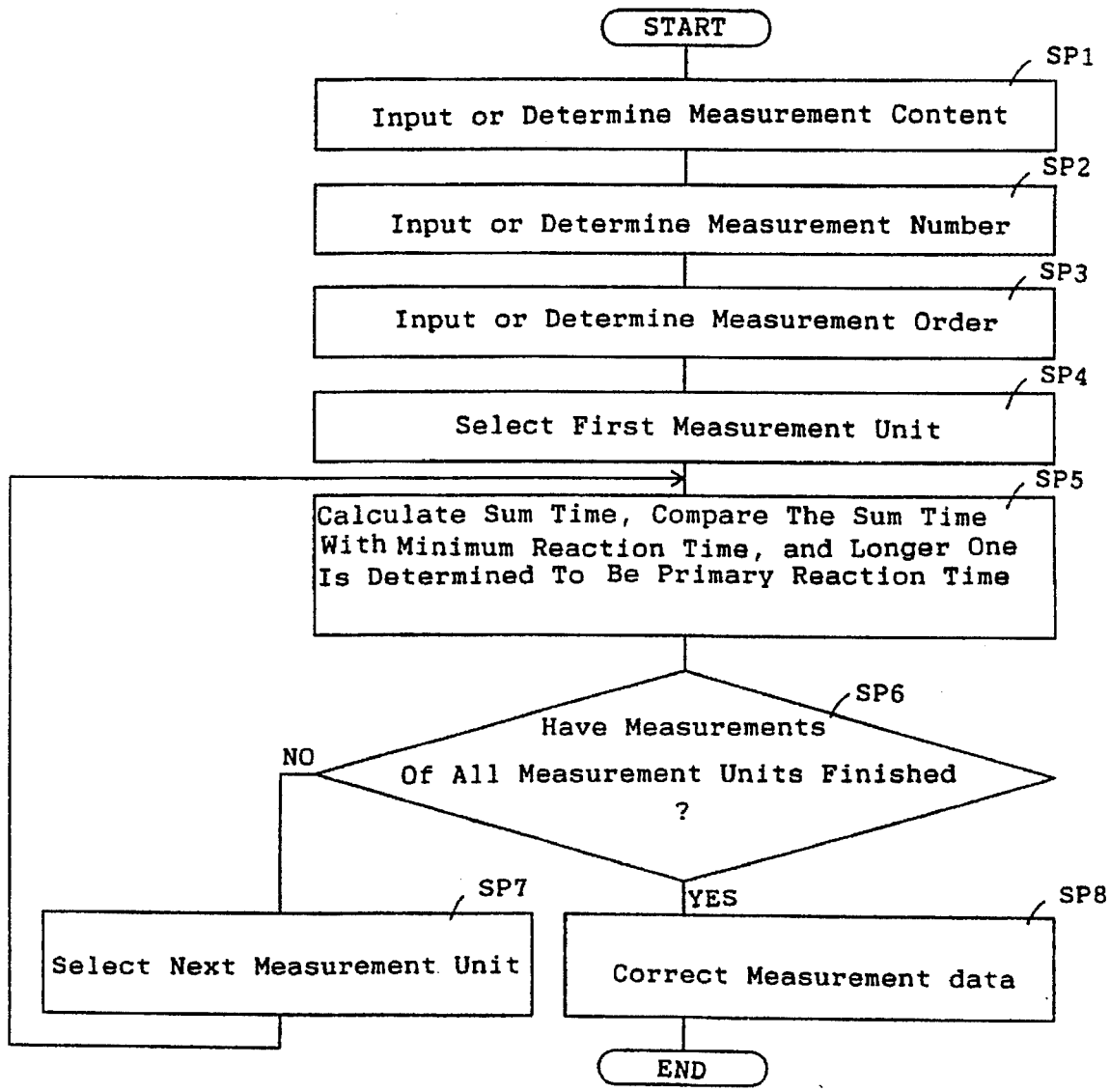
FIG. 8 is a flowchart explaining a measurement method for a fluorescent immunity measurement apparatus as a measurement time shortening method for a measurement apparatus according to second embodiment of the present invention.

FIG. 8 is a flowchart explaining a measurement time shortening method for a fluorescent immunological measurement apparatus according to a second embodiment of the present invention.

The second embodiment differs from the first embodiment in the following points.

Instead of determining the primary reaction time as in the first embodiment, the second embodiment calculates a sum of required times of pre-processings of sequential measurement units and of after-processings of sequential measurement units for each measurement unit which sequentially performs measurement processings, and between the sum time and a previously determined minimum reaction time the longer one is selected to be the primary reaction time. Measurement data is corrected after measurement so as to lessen errors caused by the difference between the reaction times of the measurement units.

In the flowchart illustrated in FIG. 8, in step SP1, when plural measurements are carried out, a measuring man inputs (or a measurement apparatus determines) which case among the case A, case B and case C types are measured. In step SP2, the measuring man inputs (or the measuring apparatus determines) a number of measurements of each of the selected cases, In step SP3, the measuring man inputs or the measuring apparatus determines a measuring order of the input or determined case A, case B, or case C types. In step SP4, a measurement unit to perform the first measurement is selected based upon the input or the determination. In step SP5, for the selected measurement unit, between (1), a sum of required times for pre-processings of the subsequent measurement units and after-processings of the preceeding measurement units, and (2) a previously determined minimum reaction time, the longer is determined to be the primary reaction time, and the measurement is carried out for the selected measurement unit. After the measurement of the selected measurement unit has finished, in step SP6, it is judged whether or not the measurements for all measurement units have been finished. When it is judged that measurements for some measurement units are not finished, in step SP7, the next measurement unit is selected and determining of the primary reaction time in step SP5 is carried out. When it is judged in step SP6 that the measurements for all measurement units have been finished, in step SP8, measurement data from the measurement units are corrected based upon the data of a standard primary reaction time when the primary reaction time is varied.

That is, this embodiment determines the primary reaction time sequentially so as not to overlap to that of another measurement unit, shortening the measurement time without division of the dilution processings in comparison with the conventional method.

In the following, it is described that the measurement method according to this embodiment can determine the measurement time to be shorter.

In the following specific measurements, 300 seconds, which is the least necessary time for reaction, is determined as the standard primary reaction time. When the sum time is shorter than 300 seconds, the primary reaction time is determined to be 300 seconds and the measurement is carried out. This determination prevents the primary reaction time from being greatly shorter than the standard primary reaction time so as to improve the correction accuracy when correction of the measurement data is carried out even when the sum times become shorter for plural measurement units when the number of measurements is small.

[When six case A types are measured]

Figure 9:
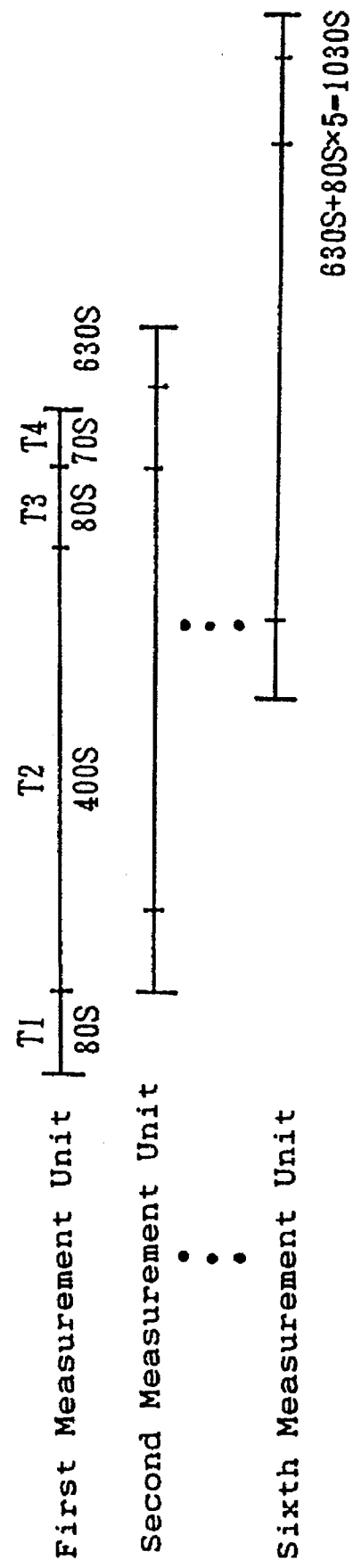
FIG. 9 is a diagram useful in understanding the measurement method of the second embodiment in the measurement time shortening method for the measurement apparatus according to the present invention.

FIG. 9 is a timechart for when six case A types are measured by determining a time interval between mesurement units to be 80 seconds. When six preparation times T1 of cases A are measured, a time of 80 seconds×5=400 seconds is necessary, thereby the primary reaction time is determined to be 400 seconds. For the first measurement unit, T1=80 seconds, T2=400 seconds, T3=80 seconds, T4=70 seconds, and the total required time is 630 seconds. And to finish the measurements from the first measurement unit to the sixth measurement unit, five measurements are carried out, each every 80 seconds sequentially from the first measurement. Therefore, the required measurement time from the beginning of the first measurement to finishing of the sixth measurement becomes 630 seconds+80 seconds× 5=1030 seconds.

[When three case B types are measured]

Figure 10:
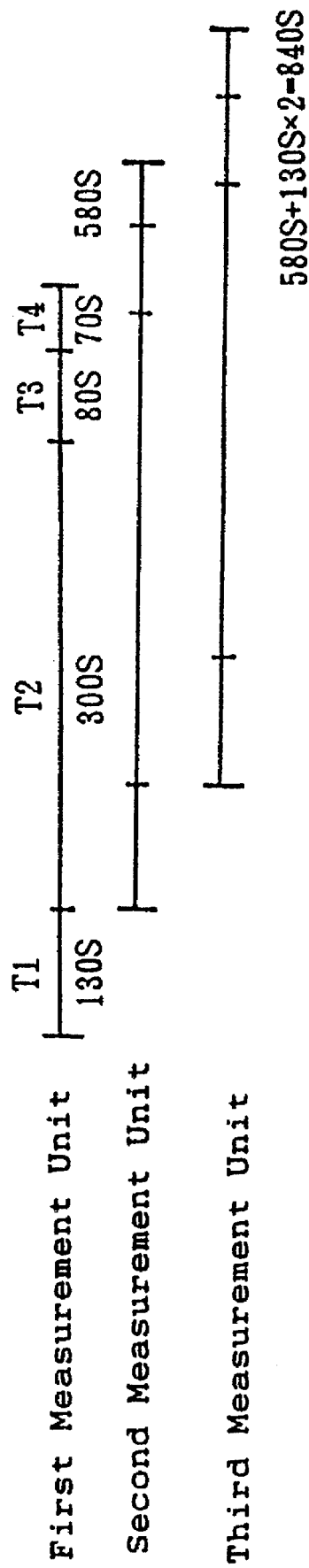
FIG. 10 is a diagram useful in understanding the measurement method of the second embodiment in the measurement time shortening method for the measurement apparatus according to the present invention.

FIG. 10 is a timechart for when three case B types are measured. When three preparation times T1 of cases B are measured, a time of 130 seconds×2=260 seconds is necessary and this is shorter than the standard time of 300 seconds, thereby the primary reaction time is determined to be 300 seconds. For the first measurement unit, T1=130 seconds, T2=300 seconds, T3=80 seconds, T4=70 seconds, and the total required time is 580 seconds. And to finish the measurements from the first measurement to the third measurement two measurements are carried out every 130 seconds sequentially after the first measurement, because the preparation time T1 of the case B is longer than the required time T3 of 80 seconds. Therefore, the required measurement time from the beginning of the first measurement to finishing of the third measurement is 580 seconds+130 seconds×2= 840 seconds.

[When six case B types are measured]

Figure 11:
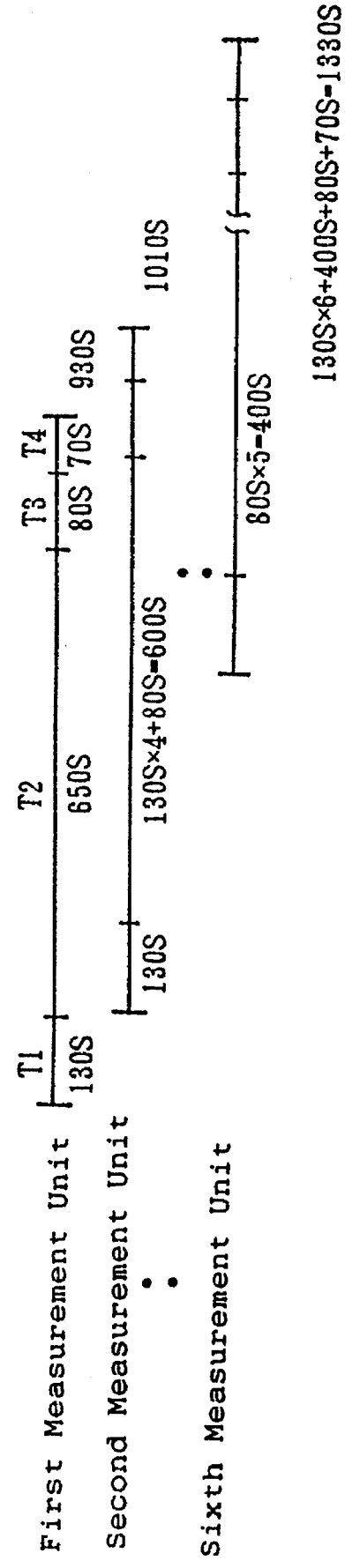
FIG. 11 is a diagram useful in understanding the measurement method of the second embodiment in the measurement time shortening method for the measurement apparatus according to the present invention.

FIG. 11 is a timechart for when six case B types are measured. In this case, the preparation time T1 of the case B is 130 seconds. When measurements are carried out using six measurement units, a time of 130 seconds×5=650 seconds is necessary, thereby the primary reaction time is determined to be 650 seconds. For the first measurement unit, T1=130 seconds, T2=650 seconds, T3=80 seconds, T4=70 seconds, and the total required time is 930 seconds. For the second measurement unit, a sum time T2=130 seconds×4+80 seconds=600 seconds, for the preparation times of the third to sixth measurement units and the T3 of the first measurement unit.

A sum time of T2=130 seconds×3+80 seconds×2=550 seconds for the third measurement unit, a sum time of T2=130 seconds×2+80 seconds×3=500 seconds for the fourth measurement unit, a sum time of T2=130 seconds× 1+80 seconds×4=450 seconds for the fifth measurement unit, and a sum time of T2=80 seconds×5=400 seconds for the sixth measurement unit are sequentially calculated by similar calculations. These sum times are longer than the standard time of 300 seconds, so each of the calculated sum times is determined as the primary reaction time for each measurement unit. Consequently, the required measurement time from the beginning of the first measurement to the finishing of the sixth measurement is 130 seconds×6+80 seconds×5+80 seconds+70 seconds=1330 seconds.

[When three case B and three case C types are measured]

Figure 12:
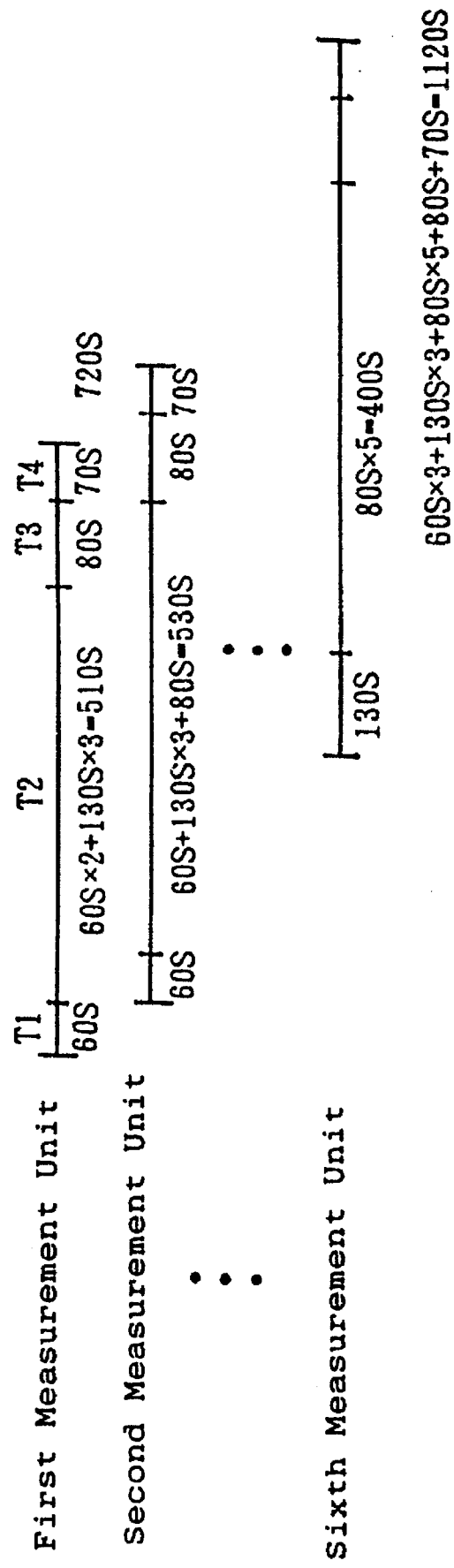
FIG. 12 is a diagram useful in understanding the measurement method of the second embodiment in the measurement time shortening method for the measurement apparatus according to the present invention.

FIG. 12 is a timechart for when three case B and three case C types are measured. It is assumed that the measuring is started using the case C. For the first measurement unit, T1=60 seconds (the preparation time for the case C), T2=60 seconds×2+130 seconds×3=510 seconds, T3=80 seconds, T4=70 seconds, and the total required time is 720 seconds. The time T2=60 seconds×2+130 seconds×3=510 seconds is obtained by calculating a sum time of pre-processings of the subsequent measurement units. For the second measurement unit, a sum time of T2=60 seconds×1+130 seconds×3+80 seconds=530 seconds, from the preparation times of the third to sixth measurement units and the after-processing time (T3=80 seconds) of the first measurement unit. A sum time of T2=130 seconds×3+80 seconds×2=530 seconds for the third measurement unit, a sum time of T2=130 seconds× 2+80 seconds×3=500 seconds for the fourth measurement unit, a sum time of T2=130 seconds×1+80 seconds×4=450 seconds for the fifth measurement unit, and a sum time of T2=80 seconds×5=400 seconds for the sixth measurement unit are sequentially calculated by similar calculations. Consequently, the required measurement time from the beginning of the first measurement to the finishing of the sixth measurement is 60 seconds×3+130 seconds×3+80 seconds×5+80 seconds+70 seconds=1120 seconds.

The measurement times according to this embodiment are collected in compared condition with the conventional examples in Table 2.

TABLE 2

| | First Embodiment | | Conventional Example | |
|---|---|---|---|---|
| | First | Sixth | | |
| Content | Measurement Slot | Measurement Slot | First Measurement Slot | Sixth Measurement Slot |
| Six cases A | 630 sec | 1030 sec | 880 sec | 1280 sec |
| Three cases B | 580 sec | 840 sec | 930 sec | 1190 sec |
| Six cases B | 930 sec | 1330 sec | 930 sec | 1580 sec |
| Three Cases C and Three cases B | 720 sec | 1120 sec | 860 sec | 1360 sec |

As is apparent from the Table 1 and the Table 2, this embodiment can finish the measurements in shorter time in comparison with the conventional measurement method and the first embodiment. Further, this embodiment has an advantage in that the dividing processing of the dilution processing in the first embodiment is not necessary. This embodiment is greatly effective when a test liquid is used which possibly causes non-specific absorption by leaving the test liquid as it is for some time period after the test liquid has been stirred.

Figure 13:
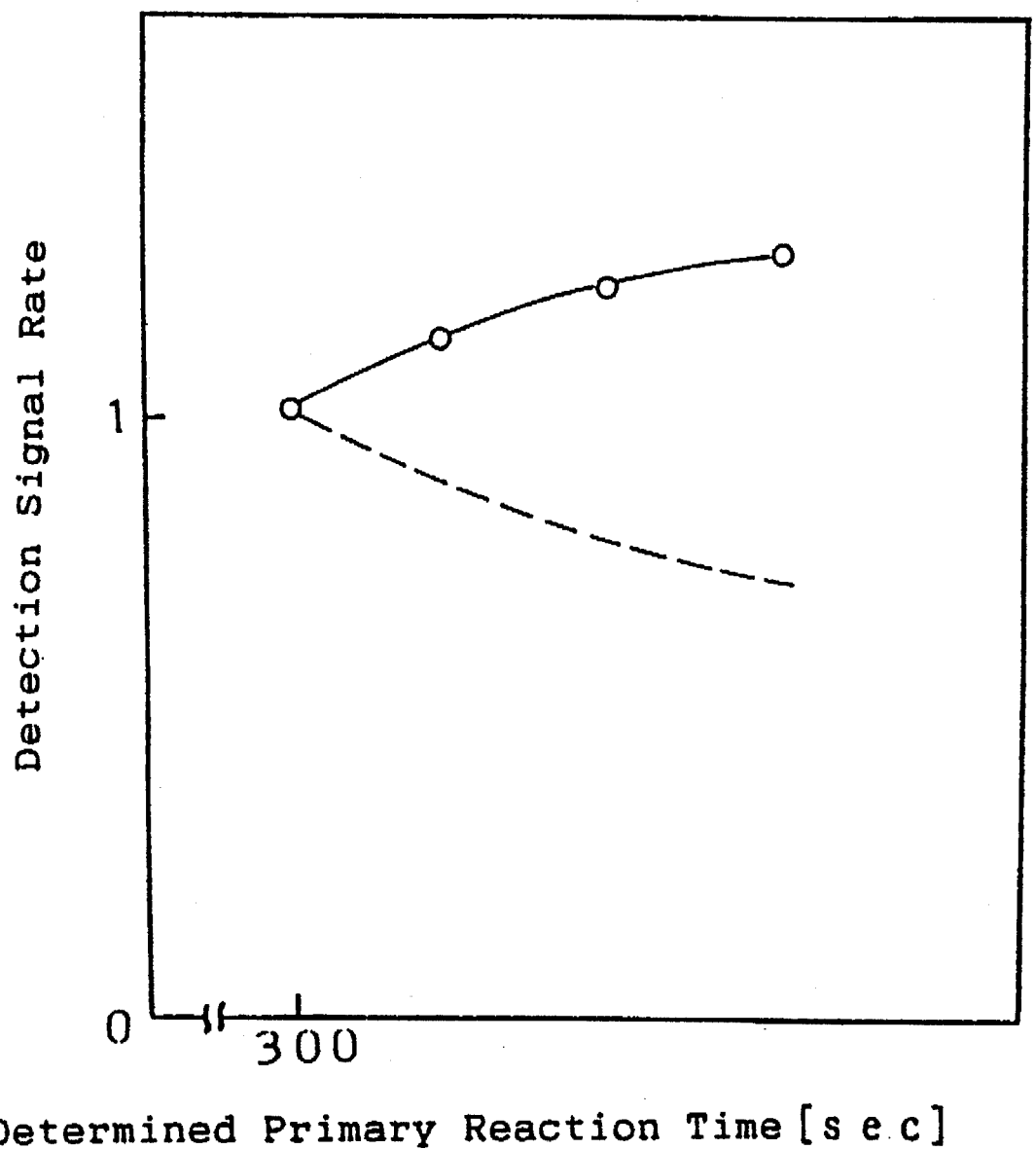
FIG. 13 is a diagram useful in understanding the correcting method of the second embodiment in the measurement time shortening method for the measurement apparatus according to the present invention.

A variation occurs in a detection signal as is illustrated in FIG. 13 with a solid line, depending upon the variation of the primary reaction time which is determined for each measurement unit. A similar tendency is developed for almost the entire region of measurement concentration. Therefore, reverse proportional data illustrated in a dashed line corresponding to the variation illustrated with the solid line is input in the fluorescent immunological measurement apparatus, and after measurement data is obtained, the measurement data is corrected using the correction data curve so that accurate measurement data is obtained.

Figure 14:
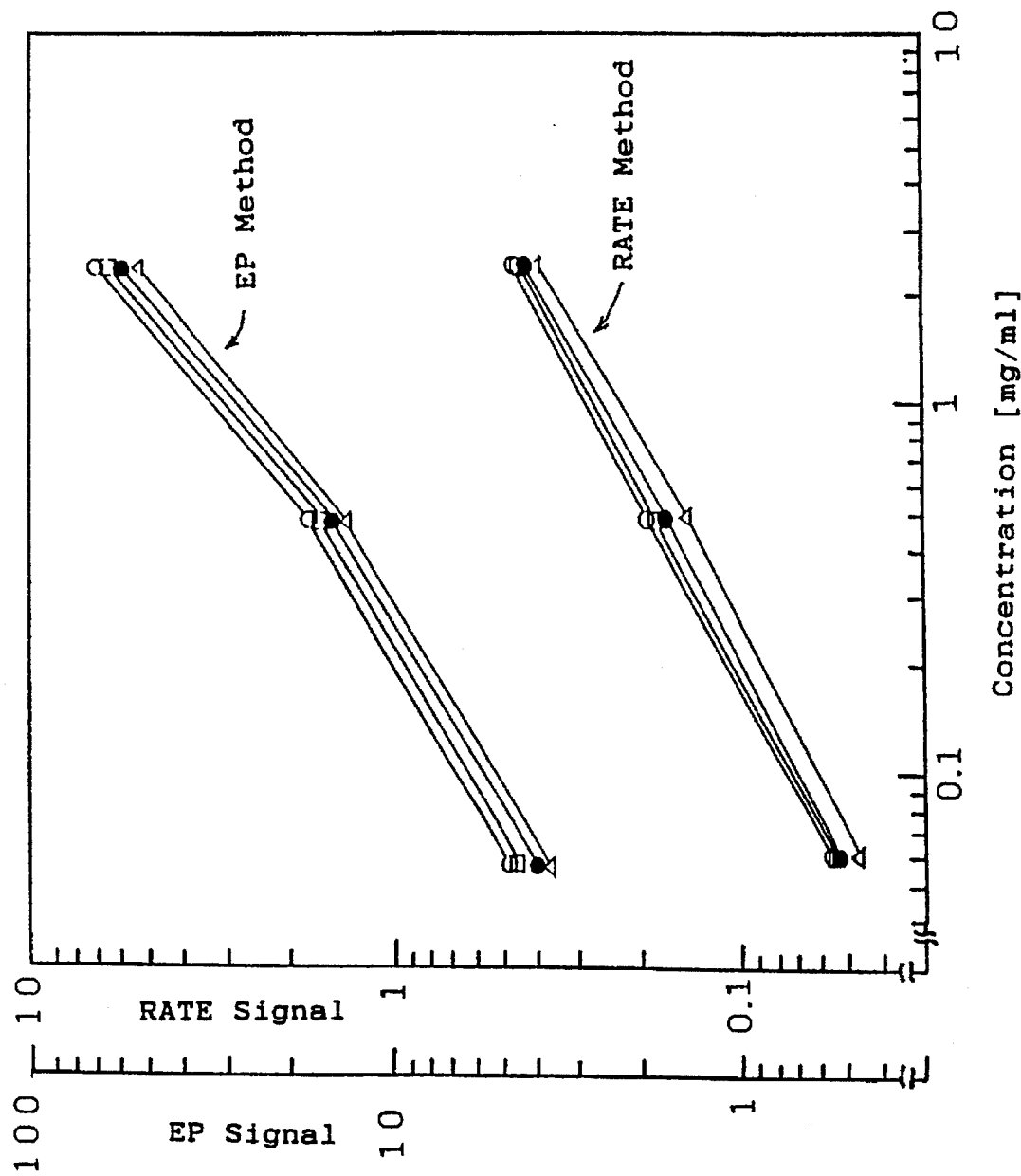
FIG. 14 is a diagram illustrating a specific example of correction of the second embodiment in the measurement time shortening method for the measurement apparatus according to the present invention.
Figure 15:
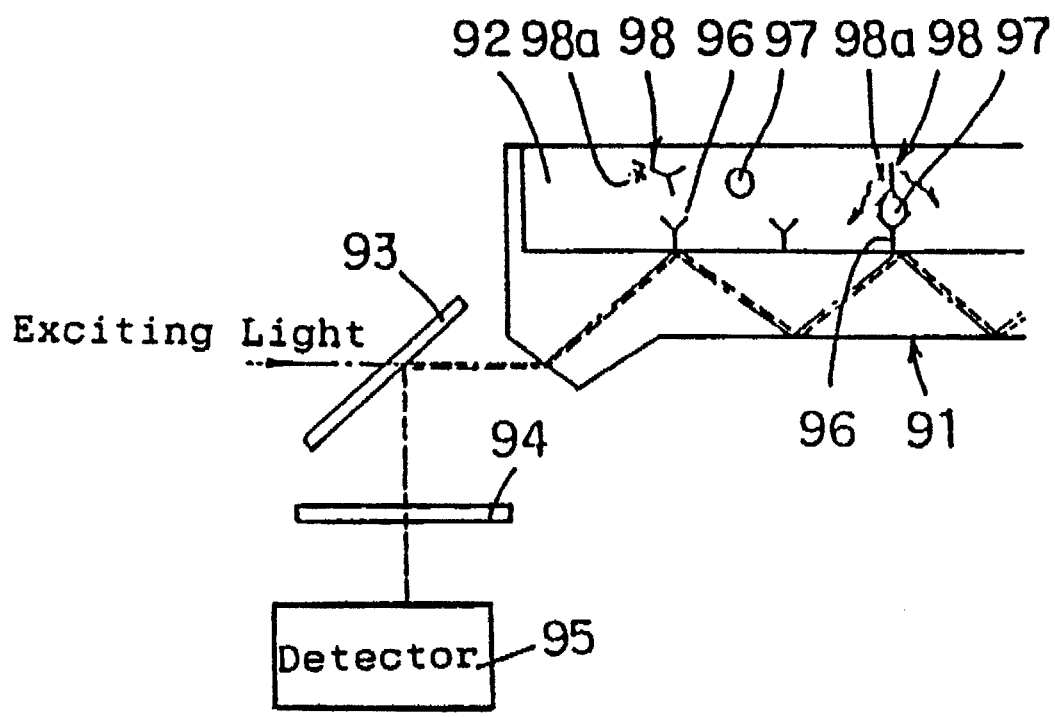
FIG. 15 is a diagram schematically illustrating a conventional fluorescent immunity measurement apparatus.
Figure 16:
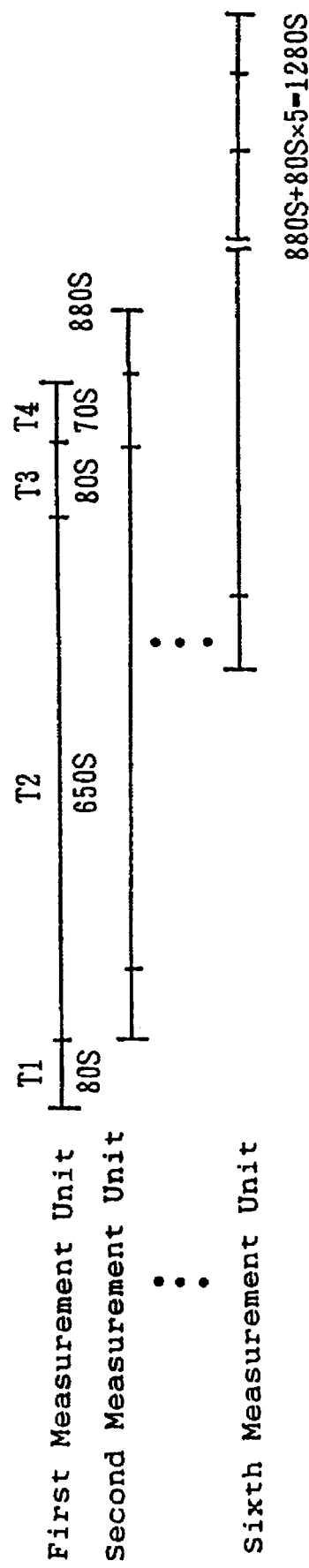
FIG. 16 is a diagram useful in understanding a measurement method of the conventional fluorescent immunity measurement apparatus.
Figure 17:
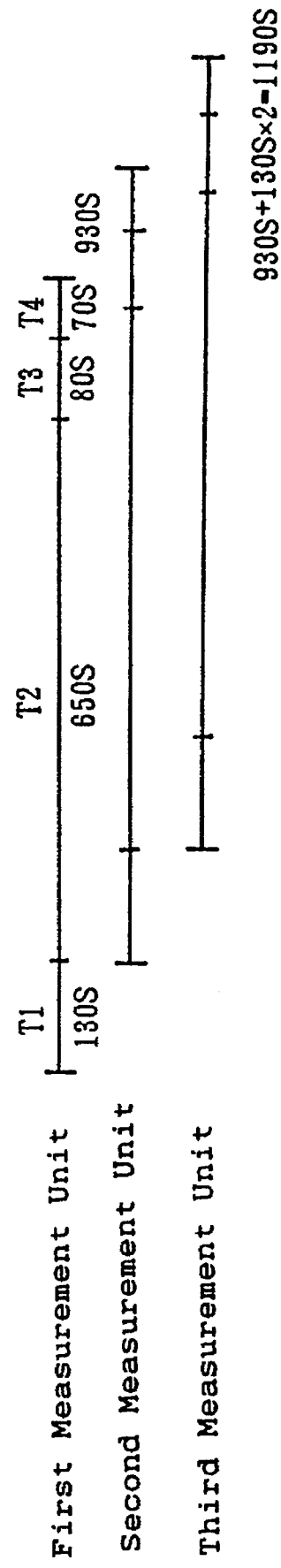
FIG. 17 is a diagram useful in understanding a measurement method of the conventional fluorescent immunity measurement apparatus.
Figure 18:
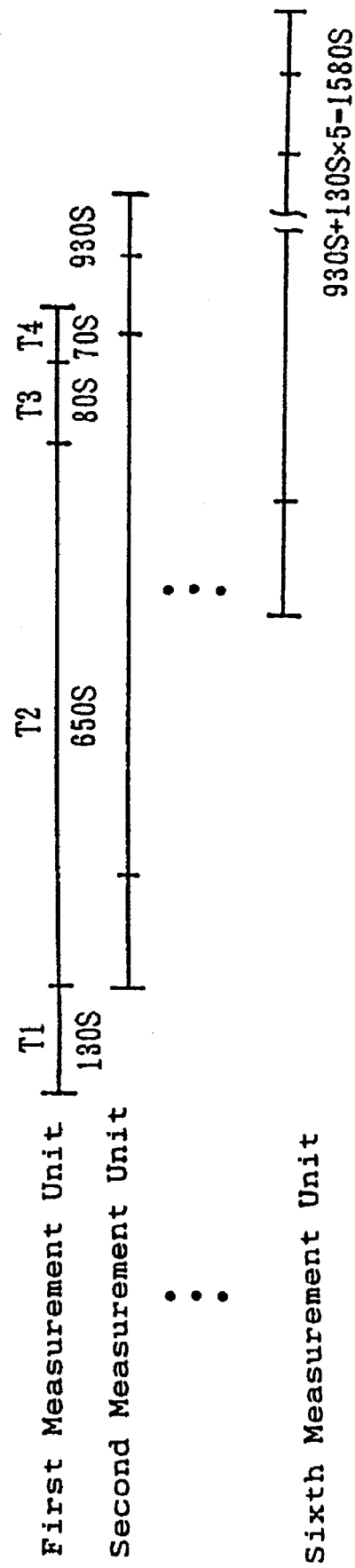
FIG. 18 is a diagram useful in understanding a measurement method of the conventional fluorescent immunity measurement apparatus.
Figure 19:
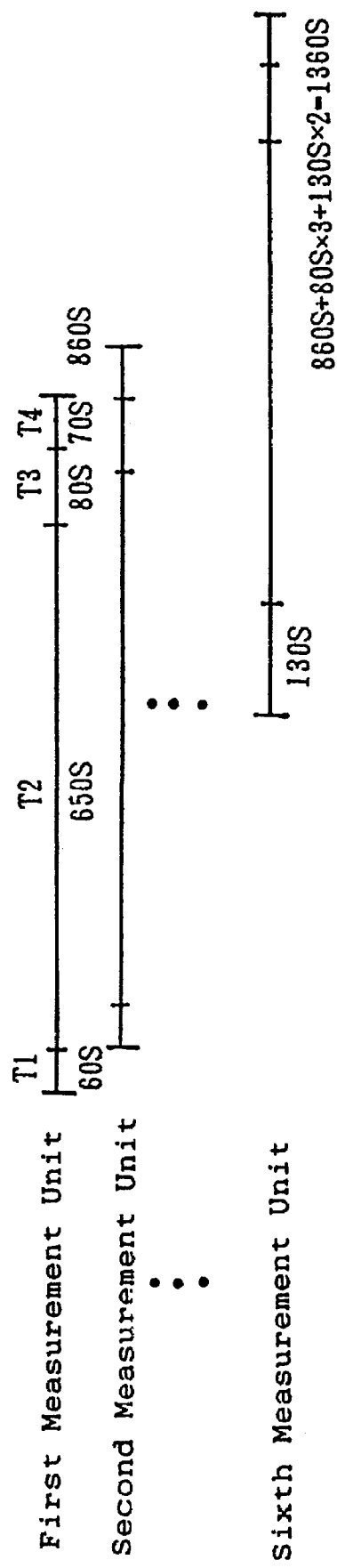
FIG. 19 is a diagram useful in understanding a measurement method of the conventional fluorescent immunity measurement apparatus.

FIG. 14 is a diagram in which signal values, which are obtained by subtracting a signal value corresponding to 0-concentration from each measured signal value which is obtained by a rate method, and an end-point (EP) method, respectively, are plotted when C-reactive-protein (CRP) is measured and the primary reaction time is determined to be 6 minutes, 8 minutes, 10 minutes, and 12 minutes. The horizontal axis indicates a concentration of CRP, the vertical axes indicate net signal values of the rate method, and the EP method. Further, triangles indicate signal values when the primary reaction time is 6 minutes, black circles indicate signal values when the primary reaction time is 8 minutes, rectangles indicate signal values when the primary reaction time is 10 minutes, and white circles indicate signal values when the primary reaction time is 12 minutes. Furthermore, the concentration of CRP is determined to be 0.05 mg/ml, 0.5 mg/ml, 2.5 mg/ml. From FIG. 14 it is understood that net signal values are properly corrected for a wide concentration extent by multiplying a constant value corresponding to the primary reaction time even when the primary reaction time is varied in the correction processing of this method, and that no problems arise in measurement even when the primary reaction time is varied in each measurement unit.

The present invention is not limited to the above-mentioned embodiments. Various modifications are applicable within an extent not to depart the scope of the present invention For example, in the first embodiment, division of the pre-processing is described by taking the example for dividing the generation of the first diluted liquid and the generation of the second diluted liquid, but dividable pre-processing is not limited to the dilution processing. Pre-processings which do not influence measurement accuracy when they are divided are able to be divided.

The present invention is applicable to a measurement apparatus which performs measurement based upon absorption, diffusion, or polarization, or to a measurement apparatus utilizing bonding reaction other than an antigen-antibody reaction or a catalytic reaction such as an enzyme-reaction when one of the measurement apparatus requires a pre-processing and an after-processing with respect to a reaction and the pre-processings and the after-processing are processed using a single processing apparatus.

Possibility of Industrial Utilization

The present invention is suitable to blood inspection and the like because a total required time is extremely shortened when measurement data of plural measurement units are obtained by performing a pre-processing, a reaction processing, and an after-processing for the plural measurement units and by performing the reaction processings in parallel with one another.

What is claimed is:

1. A method of shortening a measurement time for measuring one or more reaction processes, each of the reaction processes including a pre-processing step and a reaction step, comprising:
   determining a predetermined time for performing the reaction step;
   determining a total time required for performing each of the pre-processing steps; and
   when the total time is longer than the predetermined time,
   dividing each of the pre-processing steps into at least a first substep and a second substep, and
   carrying out at least the first substep of each pre-processing step in package prior to performing the second of each pre-processing step and the reactions steps.

2. A method of shortening a measurement time for measuring one or more reaction processes, each of the reaction processes including a pre-processing step, a reaction step, and an after-processing step, comprising, for each reaction process:
   calculating a sum of time required for performing the pre-processing steps of each subsequent reaction process and for performing the after processing steps of each preceding reaction process;
   determining a longer time between a previously determined minimum reaction time for performing the reaction step and the calculated sum time;
   performing the reaction step according to the determined longer time; and
   correcting obtained measurement data for the reaction process based upon the determined longer time.

3. A method of shortening a measurement time for measuring one or more reaction processes, each of the reaction processes including a pre-processing step and a reaction step, comprising:
   determining a predetermined time for performing the reaction step;
   determining whether the pre-processing steps can be divided into at least a first sub-step and a second sub-step;
   when the pre-processing steps can be divided into at least a first sub-step and a second sub-step, determining a total time required for performing each of the pre-processing steps; and
   when the total time is longer than the predetermined time, dividing each of the pre-processing steps into at least the first substep and the second substep, and
   carrying out the least the first substeps of each pre-processing in package prior to performing the second substeps and the reactions steps.

* * * * *